United States Patent [19]

Graham

[11] 4,208,920
[45] Jun. 24, 1980

[54] AUTOMATIC SPINNING STRENGTH TESTER

[75] Inventor: John S. Graham, Clemson, S.C.

[73] Assignee: The United States of America as represented by the Secretary of Agriculture, Washington, D.C.

[21] Appl. No.: 34,881

[22] Filed: Apr. 30, 1979

[51] Int. Cl.² ............................................. G01N 3/16
[52] U.S. Cl. ..................................................... 73/828
[58] Field of Search ................. 73/159, 160, 828, 829, 73/830

[56] References Cited

U.S. PATENT DOCUMENTS

| | | | |
|---|---|---|---|
| 1,962,020 | 6/1934 | Lee et al. | 73/829 |
| 2,142,253 | 1/1939 | Nunan | 73/829 |
| 2,875,609 | 3/1959 | Seney | 73/828 |

Primary Examiner—S. Clement Swisher
Attorney, Agent, or Firm—M. Howard Silverstein; David G. McConnell; Raymond C. Von Bodungen

[57] ABSTRACT

An apparatus for automatically testing the breaking strength of textiles during the spinning process is disclosed. A yarn clamping means affixed to a breaking assembly is rotatably mounted to an automatic timer which is pre-programmed to break yarn at set intervals. The spinning yarn is passed through a tension sensing device which measures the strength of the yarn at the breaking point, after the clamping means rotates, catches, and breaks the yarn. The clamping means then rotates back to the original position and restores and recombines the yarn as new feed yarn.

8 Claims, 4 Drawing Figures

AUTOMATIC SPINNING STRENGTH TESTER

BACKGROUND OF THE INVENTION

1. Field of the Invention

This invention relates to test equipment for measuring spinning strength of lint cotton.

2. Description of the Prior Art

There is no prior art to compare with this novel concept of measuring spinning strength. Conventional methods of studying cotton spinning quality have consisted of measuring the quality of yarn after it is spun and wound onto the bobbin and of counting the number of end breaks during the spinning process which requires lengthy tests for statistical reliability. Yarn quality measurements, particularly yarn strength, obtained from the spinner bobbin are different from those measured while the yarn is in the process of being spun and are of limited use in predicting processing performance. The strength of the yarn during spinning is very sensitive to changes in fiber properties and drafting system configuration. The development of a spinning strength tester makes it possible to measure a parameter, spinning strength, which has never been measured before. This parameter is theoretically not only highly related to spinning end breakage rate but also other characteristics of spinning systems such as the effect of roll coverings and weightings, drafting efficiency, roller and apron configurations, and fiber lubricants.

Therefore, the concept of measuring the strength of yarn while it is being spun is original. The measurement has never been studied or attempted before and provides a new approach for understanding difficult problems in cotton yarn manufacutring. It offers an opportunity to expand our basic knowledge of the drafting and spinning process and should result in significant improvement in textile technology.

SUMMARY OF THE INVENTION

The instant invention is a unique combination of mechanical elements used in combination to automatically test and measure the strength of yarn during the spinning process of textiles. The apparatus can be pre-programmed to take measurements automatically at set intervals.

A breaking assembly is mounted to a friction clutch plate. The friction clutch plate is capable of rotating the breaking assembly through about 200 degrees of rotation. A support plate is affixed to the clutch plate for rigid support of the clutch plate and the breaking assembly. A yarn clamping means is affixed to the breaking assembly and is mechanically capable of catching, applying tension, breaking, restoring and recombining a yarn strand which is fed out of a transducer through which the yarn strand passes therethrough. This tension transducer is able to measure the breaking strength of the yarn strand when the yarn clamping means applies tension and breaks the yarn strand. The tension transducer receives the yarn strand from the front drafting rolls of a conventional textile spinning process. A driving means is suitably mounted and provided to drive and rotate the friction clutch plate and in turn the breaker assembly.

DESCRIPTION OF THE PREFERRED EMBODIMENTS

In general, the spinning strength tester is programmed to automatically break and splice cotton yarn every 12 seconds as the yarn is spun on a conventional ring spinning system. Spinning strength of the yarn is measured by a suitable commercially available yarn tension transducer and a computer compatible peak meter. The yarn clamping means is affixed to a breaking assembly which is rotatably mounted and connected to an automatic timer which is preprogrammed to break yarn at set intervals. The spinning yarn is passed through a tension sensing device which measures the strength of the yarn at the breaking point, after the clamping means rotates, catches, and breaks the yarn. The clamping means then rotates back to the original position and restores and recombines the yarn as new feed yarn. A small laboratory computer can be used for collection and analysis of spinning strength distribution data for computation of the intrinsic spinning quality of cotton.

More specifically the instant invention is an apparatus comprising a breaking assembly mounted to a friction clutch plate. The friction clutch plate is capable of rotating the breaking assembly through about 200 degrees of rotation angle. A support plate affixed to the friction clutch plate is provided for rigid support. There is a yarn clamping means affixed to the breaking assembly which is capable of catching, applying tension, breaking, restoring and recombining a yarn strand automatically during the operation of the spinning process. A driving means is suitably mounted to the support plate and is also affixed to the friction clutch plate. A tension transducer through which the yarn strand passes therethrough, is able to measure the breaking strength of the yarn strand as the yarn clamping means applies tension and breaks the yarn strand which is passing through the tension transducer.

Upper and lower pin stops are provided to stop the breaker assembly when it is rotated through the 200 degrees of rotation. The breaker assembly is provided with a rubber bumber to prevent damage when brought into contact with the pin stops. The clutch plate is designed to alternately rotate in forward and reverse directions, and also uses the coasting torque to prevent rebound from rotation of the breaker assembly into the upper and lower stop pins.

Figure 1:
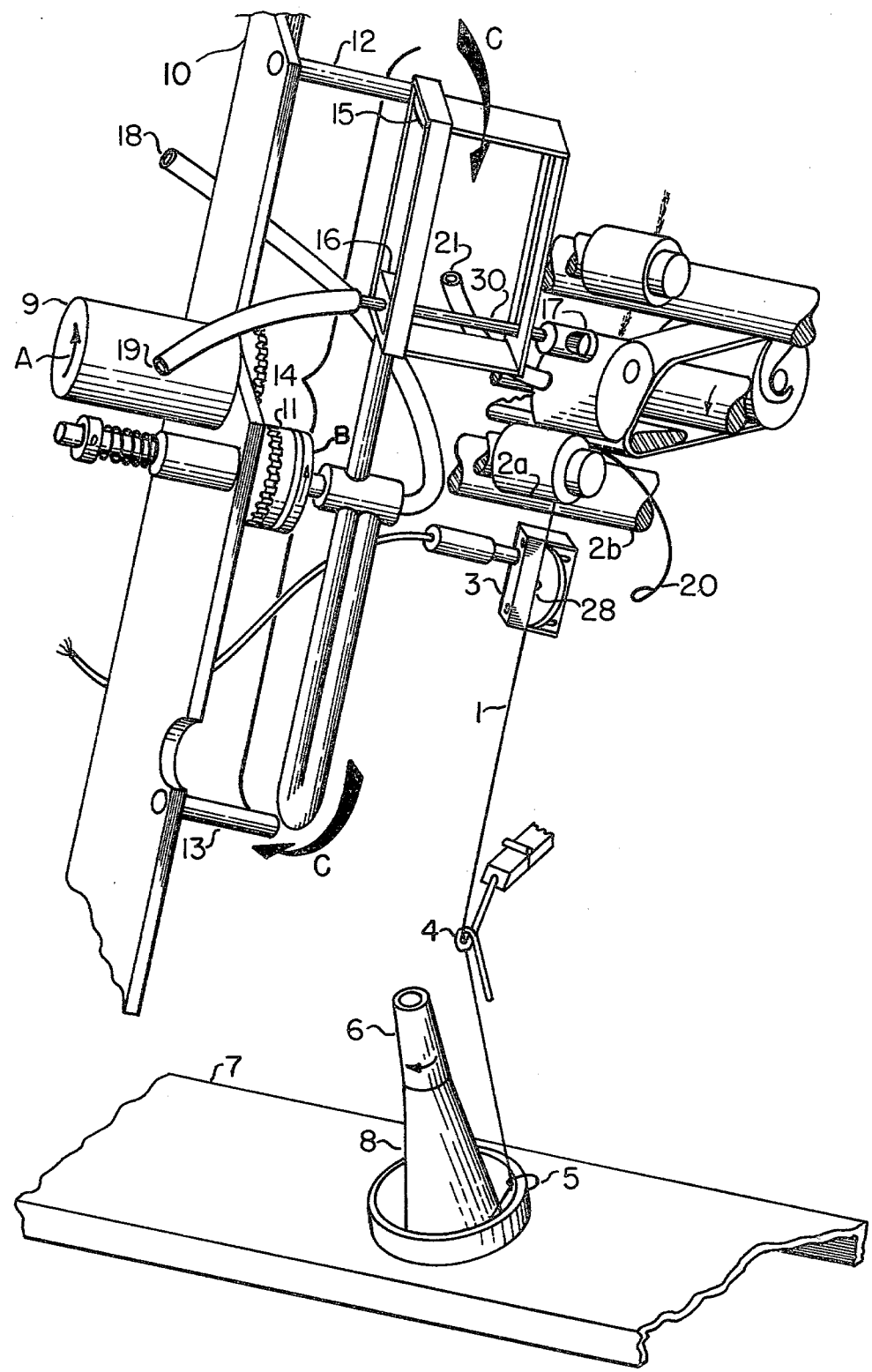
FIG. 1 is an isometric describing the initial phase of the automatic spinning strength tester.

Turning now to the specific embodiment of the invention wherein FIG. 1 shows a spinning cotton yarn strand 1 moving downward from the output of the front drafting rolls 2a and 2b, through yarn tension transducer 3 which is located just below the exit end of drafting rolls 2a and 2b. The yarn strand 1 then passes sensing pin 28 and goes through thread guide 4, (which is suitably mounted to the drafting machine) and then downward to ring traveler 5 while simultaneously being twisted and wound by spinning bobbin 6 as the vertical traverse motion of ring rail 7 controls the size and shape of yarn package 8. Tension transducer 3 is a RES Model F-21-100 yarn tension transducer having a frequency response of 10 KHz at a 3-degree yarn deflection and a load range of 0–300 grams—the angle and force range used in spinning strength tests on 40's yarn. The spinning and breaker mechanism 14 is supported by a plate 10 which is rigidly mounted in front of front drafting roll 2b, fixed longitudinally parallel to the section of the spinning yarn that lies between drafting roll 2b and yarn guide 4, traversely parallel to front drafting roll 2b. A reversible electric motor 9 mounted on support plate 10 rotates on upper friction-clutch plate 11 alternately in forward and reverse directions, through an angle of about 200° degrees. Friction clutch plate 11 protects drive motor 9 by allowing it to coast to rest after breaker 14 strikes positioning stops (upper stop 12 and lower stop 13) and uses the coasting torque to prevent rebound from these stops. The timing of the various functions of the automatic spinning strength tester is sequenced and controlled by a commercially available recycling cam timer (not shown). The cam-timer mechanism is a programmable, single cycle Model RC1 Industrial Timer. The timer is used to phase and time the yarn breaking and splicing functions of the automatic spinning strength tester. In the instant invention, switching on the relay of the timer causes the cam-shaft to make one revolution. The time for one revolution is fixed by a change gear between the electrical motor and the cam shaft. Each electrical circuit is turned on individually by the cam follower on the corresponding micro-switch, when falling into an adjustable depression in the double-disc cam. The cam depression can be fixed in any phase of the cam shaft cycle by rotating it on the cam shaft where it is held in position by friction between the cam hub and cam shaft.

Figure 2:
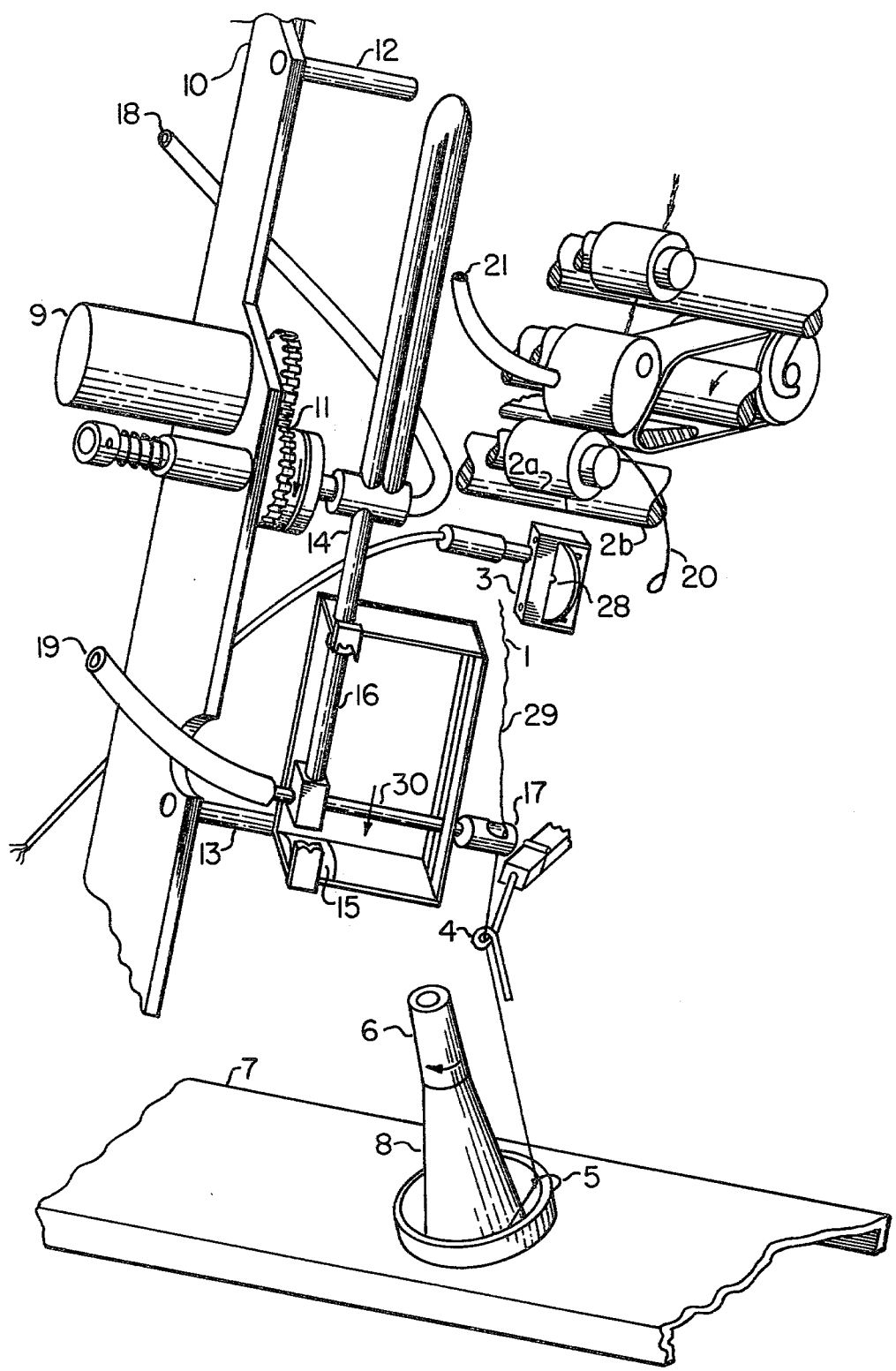
FIG. 2 is an isometric describing the second or breaking phase of the automatic spinning strength tester.
Figure 3:
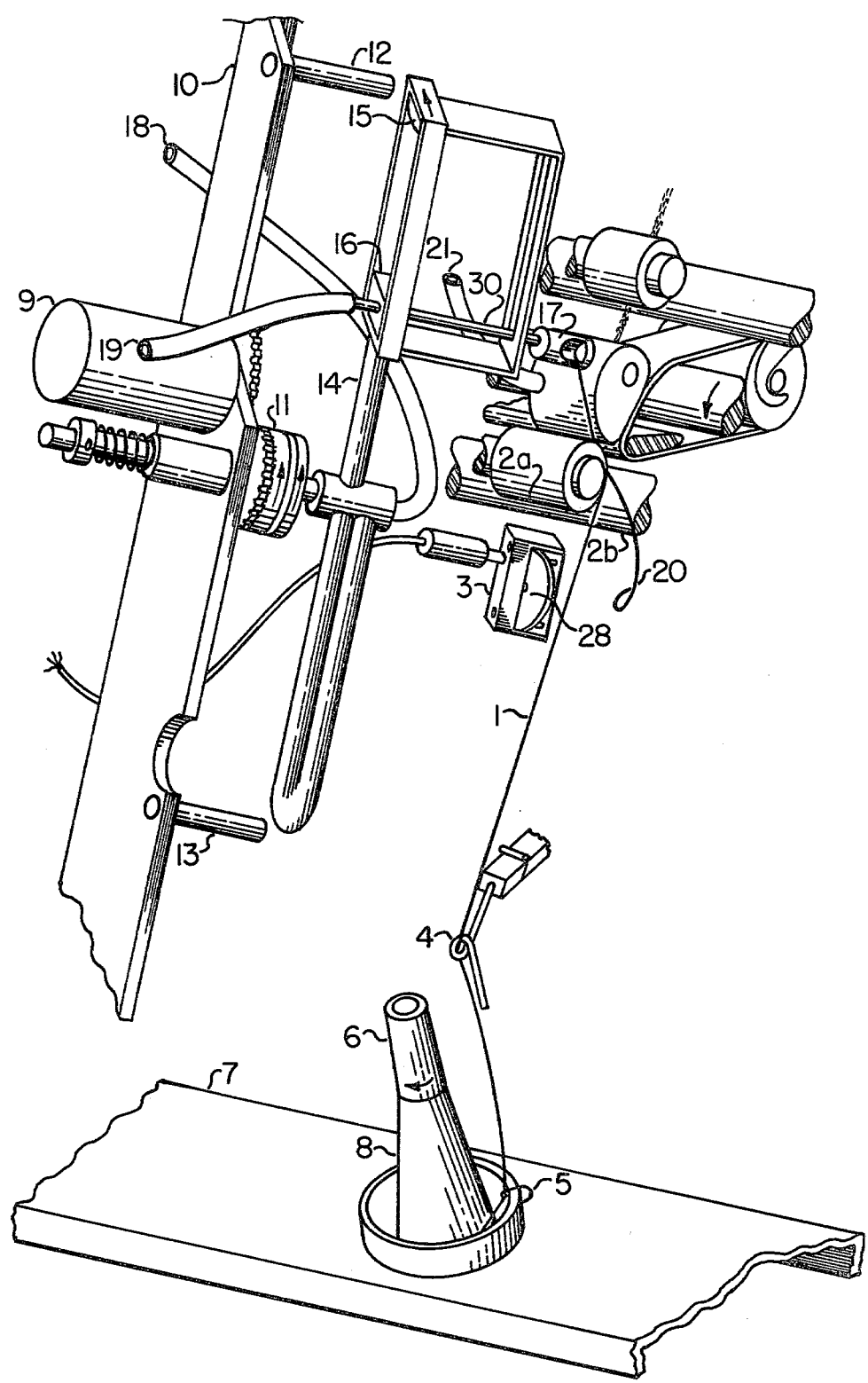
FIG. 3 is an isometric describing the third or final phase of the automatic spinning strength tester.

To break and measure the spinning yarn end, as shown in FIGS. 1, 2 and 3, the cam timer (not shown) starts motor 9 (driving means) in the counterclockwise direction, as shown by Arrow A, and viewed facing the spinning frame mechanism, rotating spinning and breaker assembly 14 through 200 degrees in the clockwise direction as shown by arrow C, to the position as shown in FIG. 2, coming to rest against lower stop pin 13 on mounting plate 10. Breaker assembly 14 has a rubber bumber 15 to prevent damage when contacting pins 12 and 13. At this point of the end-breaking cycle, breaker piston 16 which carries an air operated yarn clamping jaw 17 on the end of a pendicular extension 30 protruding below the end breaker splicer assembly 14 (see FIG. 4), has not begun its downward stroke and remains at rest holding yarn clamp 17 over the spinning yarn end, FIG. 1, just below tension transducer 3. (Which is suitably mounted but not shown). Then the programmed electrical timer (not shown) switches on an air solenoid (not shown) which admits air pressure into tube 18 connected to piston 16 and thus accelerates breaker piston 16 downward, carrying yarn clamp 17 along the travel path of spinning yarn 1. After a time interval previously programmed sufficiently for end-breaker piston 16 to accelerate to a speed of about 25 percent above the surface speed of front drafting rolls 2a and 2b, the timer (not shown) turns on another air solenoid (not shown) which supplies air pressure to tube 19 which forces a rubber bottomed yarn clamping-piston 26 (see FIG. 4) against the bottom of yarn clamp 17, thus securing the traveling yarn to the moving rubber bottomed yarn-breaker piston 26 in yarn-breaker assembly 14. The downward movement of the air operated breaker jaw depresses the yarn against sensing pin 28 in tension transducer 3 to measure the increasing spinning tension while the yarn is being strained to the breaking point, which is sensed by tension transducer 3 which transmits the analog of the breaking tension to a peak meter (not shown). The analog of the peak tension is transmitted to a digital computer (not shown) in BCD format and stored in computer memory for subsequent computation and analysis. Stress strain curves are shown on a memory scope (not shown) by synchronizing to the sweep of the memory scope with the initiation of the stroke of the breaker piston. The stress strain curves are useful for setting the time and phasing the yarn clamping and breaking cycles to protect against failure of yarn clamping jaw 17.

Immediately upon reaching the bottom of the breaking stroke, the programmed sequence timer (not shown) releases air pressure in the breaker cylinder 6 (see FIG. 4) allowing compression spring 23 to return breaker assembly 14 to the splicing position behind front drafting roll 2a as shown in FIG. 3, which is the same position resting against upper pin 12 and is the starting position while pressure is being held on yarn clamp 17, thus allowing the breaker assembly 14 to carry yarn remnant 29 upward beyond top drafting roll 2a and feeding yarn remnant 29 diagonally into the back edge of top drafting roll 2a under wire guide 20 where it is caught by the rubber surface of roll 2a and rolled into contact with the drafted fiber, thus returning strand 1 into drafting rolls 2a and 2b, and consequently restoring yarn strand 1 into the spinning process. In the absence of a spinning yarn, end fiber leaving front drafting rolls 2a and 2b is drawn into a vacuum scavenger orifice (not shown) which is located below the bottom of drafting rolls 2a and 2b.

The broken end of the yarn, remnant 29, extending from breaker jaw 17 is about 3 inches long. To prevent this yarn tail 29 from entangling in the strand being fed to top drafting rolls 2a and 2b, vacuum orifice 21 contacts this dangling tail and holds it in tension as it is released from jaw 17 by leakage of the air pressure from piston 26.

The breaking and splicing process is repeated after an 8-second period in which yarn twist in the spinning yarn end is equalized.

Figure 4:
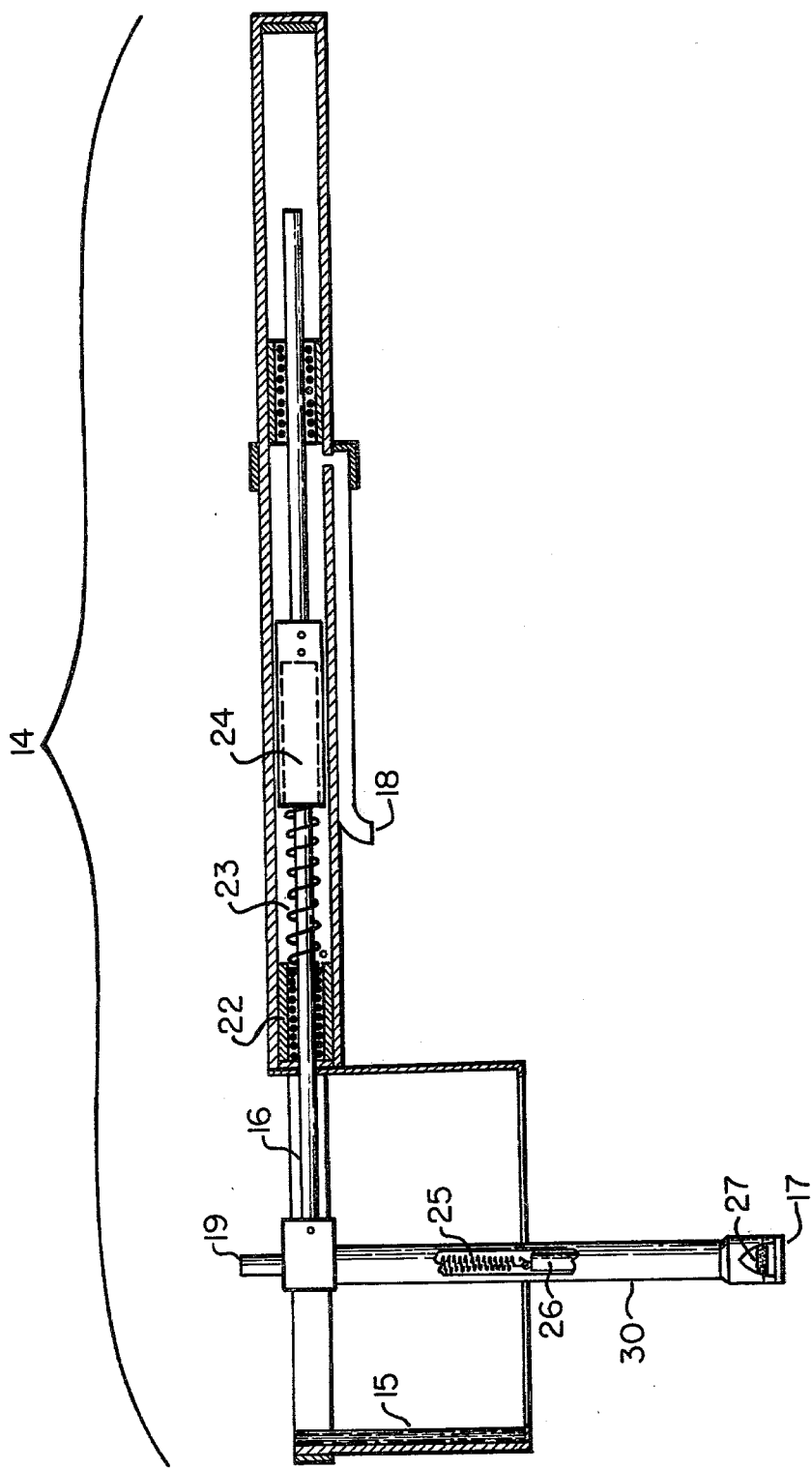
FIG. 4 is a cross-sectional view of the breaking mechanism.

Of the end-breaker designs tested, the one shown in FIG. 4 was the most successful because the breaker piston 24 slightly clears the cylinder wall and is held in alignment by the precision-ground, ¼ inch, hardened steel piston rod, supported at each end by precision ball bushings 22 which are recessed into the inside of piston 24 to maximize its length. The yarn clamp piston is suspended on the end of an expansion spring 25 in the yarn-clamp cylinder. Rubber bumper 27 stops breaker piston 24 at the end of its downard stroke.

I claim:

1. An apparatus for automatically testing and measuring the strength of yarn during the spinning process of textiles comprising in combination:
    (a) a breaking assembly mounted to a friction clutch plate, said friction clutch plate capable of rotating said breaking assembly through about 200 degrees;
    (b) a support plate affixed to said friction clutch plate for rigid support;
    (c) a yarn clamping means affixed to said breaking assembly, said yarn clamping means capable of catching, applying tension, breaking, restoring and recombining a yarn strand;
    (d) a tension transducer through which the yarn strand passes therethrough, said tension transducer able to measure the breaking strength of the yarn strand when said yarn clamping means applies tension and breaks said yarn strand passing through said tension transducer;

(e) a driving means suitably mounted to said support plate and affixed to said friction clutch plate, said driving means used to drive said friction clutch plate and thus said breaking assembly.

2. The apparatus of claim 1 including upper and lower pin stops which are used to bring said breaking assembly to a stop when said assembly is rotated for about 200 degrees.

3. The apparatus of claim 1 wherein said friction clutch plate alternately rotates said breaking assembly in the forward and reverse directions through an angle of about 200 degrees.

4. The apparatus of claim 1 wherein the breaker assembly includes a rubber bumper to prevent damage when contacting upper and lower stop pins.

5. The apparatus of claim 1 wherein the tension transducer includes a sensing pin which senses and measures the breaking strength of the yarn strand while the yarn is being strained to the breaking point.

6. The apparatus of claim 1 wherein the clamping means is air operated.

7. The apparatus of claim 2 wherein the friction clutch plate uses the coasting torque to prevent rebound from rotation of said breaker assembly into said upper and lower stop pins.

8. The apparatus of claim 6 wherein the air operated clamping means includes a rubber-bottomed yarn clamping-piston to secure the traveling yarn.

* * * * *